(12) United States Patent
Marsolek et al.

(10) Patent No.: US 9,759,708 B2
(45) Date of Patent: Sep. 12, 2017

(54) DEVICE AND METHOD TO DETERMINE, COMMUNICATE, AND DISPLAY PAVING MATERIAL TEMPERATURE

(71) Applicant: Caterpillar Paving Products Inc., Brooklyn Park, MN (US)

(72) Inventors: John Marsolek, Watertown, MN (US); Nicholas Oetken, Brooklyn Park, MN (US)

(73) Assignee: Caterpillar Paving Products Inc., Brooklyn Park, MN (US)

( * ) Notice: Subject to any disclaimer, the term of this patent is extended or adjusted under 35 U.S.C. 154(b) by 119 days.

(21) Appl. No.: 14/631,234

(22) Filed: Feb. 25, 2015

(65) Prior Publication Data
US 2016/0245785 A1    Aug. 25, 2016

(51) Int. Cl.
*E01C 19/22* (2006.01)
*G01N 33/42* (2006.01)

(52) U.S. Cl.
CPC ............. *G01N 33/42* (2013.01); *E01C 19/22* (2013.01)

(58) Field of Classification Search
CPC ...... E01C 19/004; E01C 19/288; E01C 19/48; E01C 19/22; G01N 25/00; G01N 33/42; G06F 19/00
See application file for complete search history.

(56) References Cited

U.S. PATENT DOCUMENTS

| | | | | |
|---|---|---|---|---|
| 5,942,679 A | * | 8/1999 | Sandstrom | E01C 19/26 404/133.05 |
| 6,749,364 B1 | * | 6/2004 | Baker | E01C 19/288 404/118 |
| 8,099,218 B2 | * | 1/2012 | Glee | E01C 19/004 106/271 |
| 8,382,395 B2 | * | 2/2013 | Glee | E01C 19/004 404/78 |
| 2009/0317186 A1 | * | 12/2009 | Glee | E01C 19/004 404/75 |
| 2013/0290062 A1 | | 10/2013 | Patel et al. | |
| 2016/0042235 A1 | * | 2/2016 | Buschmann | G06T 7/0004 348/148 |
| 2016/0076205 A1 | * | 3/2016 | Corcoran | E02D 3/026 73/784 |

* cited by examiner

Primary Examiner — Abigail A Risic
(74) Attorney, Agent, or Firm — Miller, Matthias & Hull

(57) ABSTRACT

A device and method of communicating the temperature of paving material on a surface, including receiving temperature and position information of a portion of the paving material, determining a plurality of predicted temperatures of the paving material each associated with a plurality of positions of the paving material with a temperature and positional model, and displaying the plurality of predicted temperatures of the paving material at the plurality of positions of the paving material with respect to at least one machine.

20 Claims, 7 Drawing Sheets

DEVICE AND METHOD TO DETERMINE, COMMUNICATE, AND DISPLAY PAVING MATERIAL TEMPERATURE

TECHNICAL FIELD

The disclosure relates generally to devices and methods used in paving, and relates more particularly to devices and methods used in paving for determining, communicating, and displaying position and temperature data of paving material during paving for use in guiding paving operations and improving paving performance.

BACKGROUND

A wide variety of machines for paving and compacting paving materials such as asphalt have been used for decades. The term "asphalt" is used broadly herein in reference to the class of paving materials consisting of aggregate mixed with one or more viscous materials such as petroleum-derived asphalt, other definitions for "asphalt" notwithstanding. A conventional approach for paving a surface such as a road or parking lot is to distribute hot paving material onto a prepared bed with a paving machine, then follow the paving machine with one or more compacting machines to compact the material to a desired density and obtain an acceptable surface finish. Most commonly, the compacting process is performed with double drum compacting machines, having a front drum and a back drum, which serve to propel the machine and compact the asphalt to a suitable state via the weight of the compacting machine, often in cooperation with drum vibrating apparatuses. Completing compaction can often require multiple passes across the asphalt mat with the compacting machine.

A typical system for paving a work area such as a parking lot or road can include numerous different machines. Supply machines such as haul trucks may be used to deliver paving material for distribution and compaction on a work surface. The paving machines may be supplied directly from the haul trucks, or from material transfer vehicles. The paving machines typically distribute paving material and perform a preliminary compaction of a "mat" of paving material with a screed mounted at a back end of the paving machine. In many systems, the paving machine is followed relatively closely by a compacting machine known in the art as a breakdown roller. Another compacting machine known as an intermediate roller often follows the breakdown roller, and a final finish roller may follow behind the intermediate roller in some systems. Various factors can affect the efficiency and success of a paving job, such as operator experience with the various machines, environmental conditions and temperature of the paving material at different stages of the paving process. Working paving material under optimum temperature conditions has long been recognized as important, but has before now been difficult to ensure and verify without manual measurements by support personnel.

Paving material is typically obtained at a relatively high temperature at an asphalt plant. Depending in part upon the distance a supply machine has to travel to reach a work site, traffic, ambient temperature, etc., the asphalt can cool somewhat prior to delivery. Progress of the paving machines and compacting machines can also vary, and haul trucks may have to wait to offload the paving material if paving has slowed. The manner in which paving material is delivered to a paving machine can also vary among systems, e.g. via a material transfer vehicle or "MTV" versus direct delivery from a haul truck. Due to the variables which can affect the timing of the various events in a paving process, a temperature of the paving material when it eventually reaches the paving machine can be at least somewhat unpredictable.

Once transferred into a paving machine, paving material will tend to cool further, prior to being distributed onto a work surface. The extent of cooling, once within the paving machine, can vary depending on the temperature of paving material at delivery, environmental factors, proper versus improper operation of the paving machine, etc. In some instances, paving material may segregate within a paving machine, and thus relatively cooler and relatively warmer pockets of material within the machine may exist, leading to unexpected temperature gradients in the paving material once distributed on the work surface. When paving material is finally discharged and distributed by the paving machine, treated via its screed, and ready to be compacted by the various compacting machines, its temperature can vary significantly from an expected temperature, and may even be non-uniform from one paved region to the next due to unintended segregation or poor mixing. As alluded to above, being able to work paving material under certain conditions such as optimum temperature can often be of paramount importance.

For example, depending upon the particular mix of paving material, it may have a temperature range known in the art as the "tender zone" where attempted compacting is unlikely to succeed. When paving material temperature is in the tender zone it may be prone to shoving and, as a result, there may be a "wave" in front of the compacting machine drum. It is well known in the paving arts that successful compaction may take place in one of potentially multiple "optimal temperature zones" when the paving material temperature is either above the tender zone or below the tender zone but above a minimum temperature. Ideally, breakdown rollers, mentioned above, follow the paving machine closely enough that they compact paving material prior to its cooling to the tender zone or the minimum temperature. Intermediate rollers typically follow sufficiently far behind the breakdown roller that the paving material has cooled below the tender zone by the time the intermediate roller reaches a particular stretch of paving material. It is also typically desirable to employ the finish roller prior to paving material cooling to below a minimum temperature at which the paving material becomes too hard.

Sticky, viscous properties of hot paving material can cause it to adhere to paving and compacting equipment where relatively cool machine components come into contact with the paving material. This tendency for hot paving material to stick to machine surfaces is generally a function of the heat transfer out of the paving material. The paving material may congeal and increase in viscosity where it is cooled by contact with machine surfaces. The greater the difference in temperature between the paving material and machine surfaces, the greater the tendency for paving material to stick.

As paving material is laid down by a paver, a component of the paver known as a screed is typically used to prepare the paving material for compacting. Screeds commonly include a metallic implement having a surface which slides across a pile of paving material deposited on a work surface to level and slightly compact the paving material in anticipation of further working by a compacting machine. The efficacy of the screed and ultimately quality of the paving job may be affected where paving material adheres to the screed instead of smoothly slipping past the screed surfaces. In other words, paving material stuck to the screed can affect the ability of the screed to provide a paving material mat suitable for finishing with a compacting machine. Irregularities in the paving material mat laid down in advance of the compacting machine(s) can result in unevenness in the later compacted surface.

In addition to the challenges to successfully paving in the first place, many jurisdictions now mandate logging data relating to paving material temperature and machine activities during a paving operation. Records of such operations at a paving site allow paving contractors to establish that paving was performed within specifications, and are commonly related to contract validation and bonuses as well as predictive and forensic aspects of construction. Standard procedure for this type of data logging has heretofore relied principally on manual observation and recording of the temperature of paving material while working a particular area.

One way of monitoring pavement temperature for compaction operations is disclosed in U.S. Pat. No. 6,749,364, entitled "Temperature Sensing for Controlling Paving and Compaction Operations." U.S. Pat. No. 6,749,364 discloses a pavement temperature monitoring system on a paver vehicle with a temperature sensor and a display device which can receive an electrical signal sent by the temperature sensor and generate a graphical image corresponding to the signal.

Accordingly, what is needed is a device and method to determine, communicate, and display the temperature of paving material in conjunction with a predictive temperature and positional model to operators of paving and compacting machines.

SUMMARY

In one aspect, a device is configured to determine and display a predicted temperature of a paving material at a plurality of positions is disclosed, the device including a processor configured to receive temperature and position information of a portion of the paving material, the processor further configured to determine a plurality of predicted temperatures of the paving material with a temperature and positional model, each of the plurality of predicted temperatures associated with a plurality of positions of the paving material, and a display configured to show the plurality of predicted temperatures of the paving material at the plurality of positions of the paving material with respect to at least one machine.

In another aspect, a method of determining and displaying a predicted temperature of a paving material at a plurality of positions is disclosed, the method including receiving temperature and position information of a portion of the paving material with a processor, determining a plurality of predicted temperatures of the paving material each associated with a plurality of positions of the paving material with a temperature and positional model with the processor, and displaying the plurality of predicted temperatures of the paving material at the plurality of positions of the paving material with respect to at least one machine with a display.

DETAILED DESCRIPTION

Figure 1:
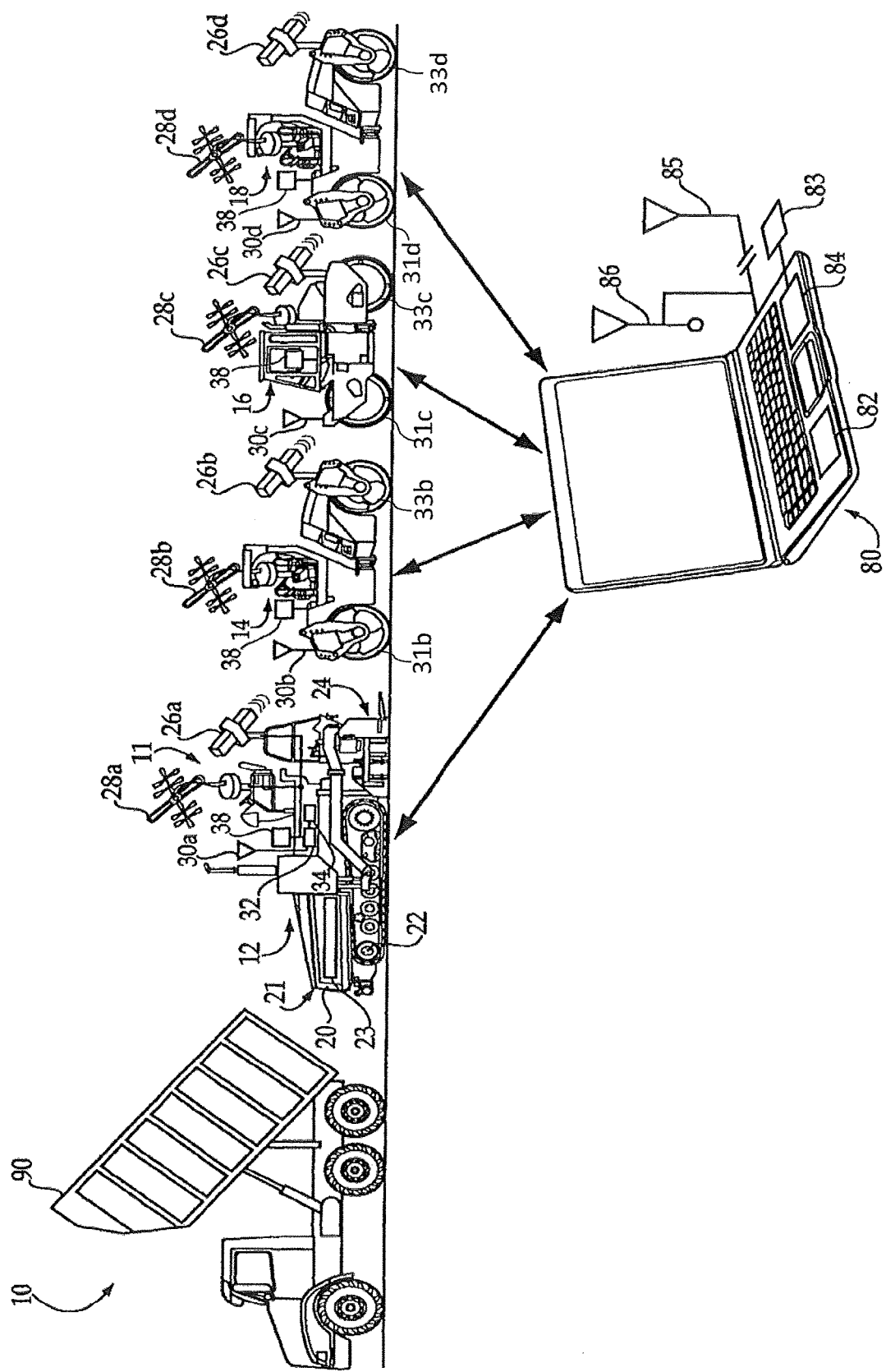
FIG. 1 shows a system in which a paving machine lays a paving material on a surface to be compacted by multiple compacting machines, according to an aspect of the disclosure.

FIG. 1 shows an operation in which a paving machine lays a paving material on a surface to be compacted by multiple compacting machines, according to an aspect of the disclosure. Referring to FIG. 1, there is shown a paving operation 10 according to the disclosure. The paving operation 10 may include one or more machines, for example a plurality of different machines, or even a plurality of identical machines in certain aspects. Each of the machines of the paving operation 10 is configured to interact with a paving material, typically performing a particular type of work thereon. In one exemplary aspect, the paving operation 10 includes a paving machine 12, and three compacting machines 14, 16, and 18. The compacting machines 14, 16, and 18 can be asphalt compactors, pneumatic compactors, or the like, and may each have a front ground engaging member 31$b$-$d$, a rear ground engaging element 33$b$-$d$, and a power source (not shown) that may drive the front ground engaging member 31$b$-$d$ and/or the rear ground engaging element 33$b$-$d$. One or more supply machines 90, such as a haul truck, a material transfer vehicle, etc., may be provided which supply paving material to the other machines of the paving operation 10 for paving a work surface.

While only certain machines are shown, it should be appreciated that for relatively large paving jobs, additional paving machines 12, additional compacting machines 14, 16, and 18, additional supply machines 90, etc. may be part of the paving operation 10. Moreover, while in many aspects the paving operation 10 will be used in paving one particular work area, such as a stretch of road, a parking lot, etc., in other aspects, additional machines at other work areas may be part of a large integrated paving operation that includes the machines of the paving operation 10 shown in FIG. 1. For example, two or more "paving trains" each having a plurality of machines, located on different sections of a road might all fairly be considered part of one paving operation as contemplated herein. In still other aspects, the determination, communication and display aspects of the disclosure may be embodied in a paving operation having only a single machine. In all versions, the disclosure is considered to provide substantial advantages over state of the art paving operations with regard to real time optimization for paving quality and forensic and predictive analysis of paving parameters, as further described herein.

In the illustrated aspect, the paving machine 12 may include a frame 20 having a set of ground engaging elements 22 (e.g., wheels or tracks) mounted thereto, as well as a screed 24 for working paving material in a conventional manner. The paving machine 12 may further include a hopper 21 for storing paving material supplied via supply machine 90 or another supply machine and a conveyor system 23 which may transfer paving material from the hopper 21 to the screed 24. The paving machine 12 may further include a receiver 28a mounted to the frame 20 which can receive electronic signals including position data for the paving machine 12. Position data received via the receiver 28a may include geographic position data such as Satellite Positioning System signals as defined herein, local positioning signals, or position data indicative of a position of the paving machine 12 relative to other machines of the paving operation 10. Alert commands, navigation commands such as start commands, stop commands, machine speed commands, conveyor speed commands, travel direction commands, etc., may also be received via receiver 28a, as well as data signals from other machines of the paving operation 10 including paving material temperature data and machine position data as described herein. The paving machine 12 may further include a signaling device such as a transmitter 30a for outputting data signals, outputting control signals to other machines, or the like, mounted to frame 20. A display device 38, such as a liquid-crystal display (LCD) device, may be mounted to the frame 20 or positioned elsewhere on the paving machine 12 for viewing by an operator. It should be noted, that the receiver 28a and the transmitter 30a may be combined as a transceiver.

In one aspect, the display device 38 may be configured to display a map of a work area, including icons, paving material temperature, etc. representing one or more of the machines of the paving operation 10 relative to temperature zones of the paving material on the surface to which the paving material is being applied. The display device 38 may be a cathode ray tube (CRT), a light-emitting diode display (LED), an electroluminescent display (ELD), a plasma display panel (PDP), an LCD, an organic light-emitting diode display (OLED), or any other display technology. The information may be displayed simultaneously or the user may interact with an input device such as buttons or, if the display is a touch-screen, with icons on the display to cycle through the various types of information for display. The display device 38 may be a touchscreen. In an exemplary aspect, the touchscreen display may detect a presence and location of a touch of a user within the display area. For example, touching the display device 38 with a finger, stylus, or hand.

In one operation, the display device 38 may show various objects associated with applications for execution. For example, a user may touch the display device 38 to interact with objects on the display device 38. That is, touching an object may execute an application associated with the object that is stored in the computer readable medium or memory 34. Additionally or alternatively, touching an object may open a menu of options to be selected by the user. The display device 38 may include a plurality of objects for a user to interact with. Moreover the display device 38 may include a plurality of screens, the display device 38 showing one screen at a time. The user may interact with the display device 38 to move a screen into view on the display device 38. Various objects may be located in each of the screens. The touchscreen display may be implemented as a resistive touchscreen, a surface acoustic wave touch screen, a capacitive touchscreen, self-capacitance sensors, infrared sensors, dispersive signal technology, acoustic pulse recognition, or the like.

The display device 38 may be generally configured to display a graphical user interface (GUI) that provides an easy to use visual interface between a user and the operating system or application(s) running on the display device 38. Generally, the GUI presents programs, files and operational options with graphical images. During operation, the user may select and activate various graphical images displayed on the display device 38 in order to initiate functions and tasks associated therewith.

The display device 38 may also be configured to display temperature and position of paving material in a work area, for reasons which will be apparent from the following description. The temperature and position information may show temperature zones corresponding to the temperature of the paving material at various locations, along with the location of the paving machine 12 and the compacting machines 14, 16, and 18. The temperature and positional information may be based solely on the temperature of the paving material at given locations, or it may also consider the composition of the paving material, its temperature when picked up from the supplier, time until delivery, the mat thickness, the ambient air temperature, underlying soil or other substrate temperature and moisture content, wind speed, solar gain, precipitation, air humidity, whether paving material is delivered directly to paving machines from haul trucks, and the like. The temperature and positional information may be automatically determined and updated based on the sensing of relevant data, or may be input to the display device 38, and based on a positional temperature model. The position and temperature data may be transmitted to the display device 38, and the display device 38 may convert the data into a display on the display device 38. This process may be repeated to continuously or periodically determine the temperature and position model.

A computer readable medium or memory 34, such as RAM, ROM, flash memory, a hard drive, etc., may also be mounted to the frame 20 or elsewhere on paving machine 12. In one aspect, the computer readable memory 34 may have program instructions including computer executable code recorded thereon for carrying out one or more of the control functions of the disclosure, further described herein. The computer readable memory 34 may also be configured to have electronic data associated with operation of the paving operation 10 recorded thereon via a memory writing device, including temperature data for paving material with which the paving operation 10 interacts, position data, time data, and lift number data for example. In one aspect, the computer readable memory 34 may have temperature data collected from a temperature sensor 26a, mounted for example on the screed 24, recorded thereon during operation, as well as machine position data received via the receiver 28a. The sensor 26a may include an optical temperature sensor such as an infrared camera whereas in other aspects the sensor 26a may include a non-optical sensor such as a digital or analog thermometer. The sensor 26a may be analog or digital, and may be a thermistor, thermocouple, infrared camera, infrared sensor integrated circuit, or the like. Moreover, the sensor 26a may be implemented as a plurality of sensors.

While the sensor 26a is shown mounted above the screed 24, so that it can scan paving material temperature deposited on a work surface, and located behind the screed 24 as paving progresses, the disclosure is not thereby limited. In other aspects, the sensor 26a might be mounted at a different location on the paving machine 12, and may even sense paving material temperature within the paving machine 12. The sensors 26b, 26c, and 26d, for example, may be mounted on the compacting machines 14, 16, and 18 to sense the temperature of paving material as the compacting machines 14, 16, and 18 pass over the paving material. Furthermore, each of the sensors 26a, 26b, 26c, and 26d may each be implemented as a plurality of sensors obtaining temperature from a plurality of different areas.

A paving control system 11, of which computer readable memory 34 may be a part, may also be provided, which includes an electronic control unit 32 coupled with each of the receiver 28a, the transmitter 30a, the display device 38, the memory 34, and the sensor 26a. The electronic control unit 32 may include a control module which includes the memory writing device mentioned above. The paving control system 11 is described in more detail below.

Figure 4:
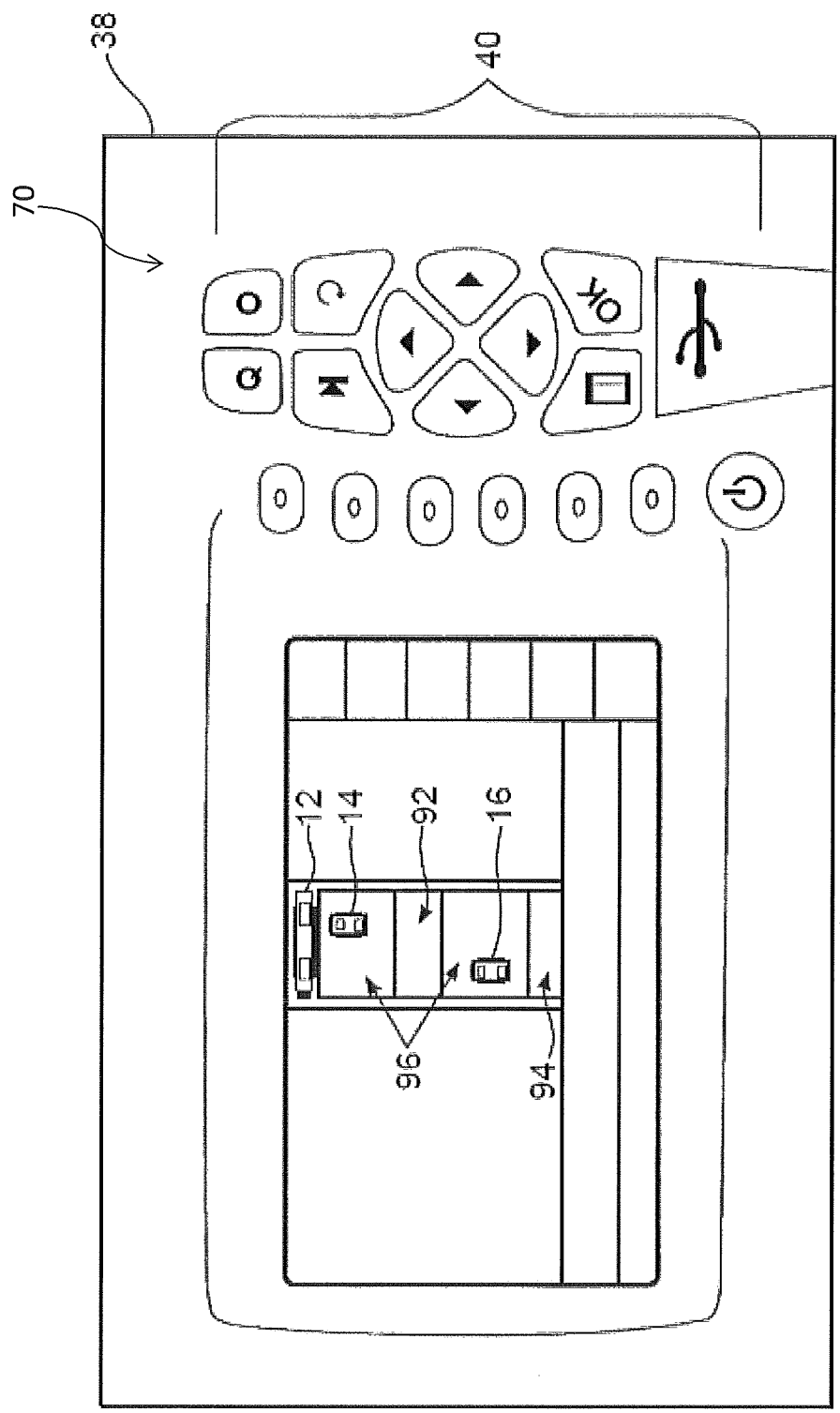
FIG. 4 shows an operator interface with a display device depicting temperature zones and the paving and compacting machines relative to the temperature zones, according to an aspect of the disclosure.
Figure 7:
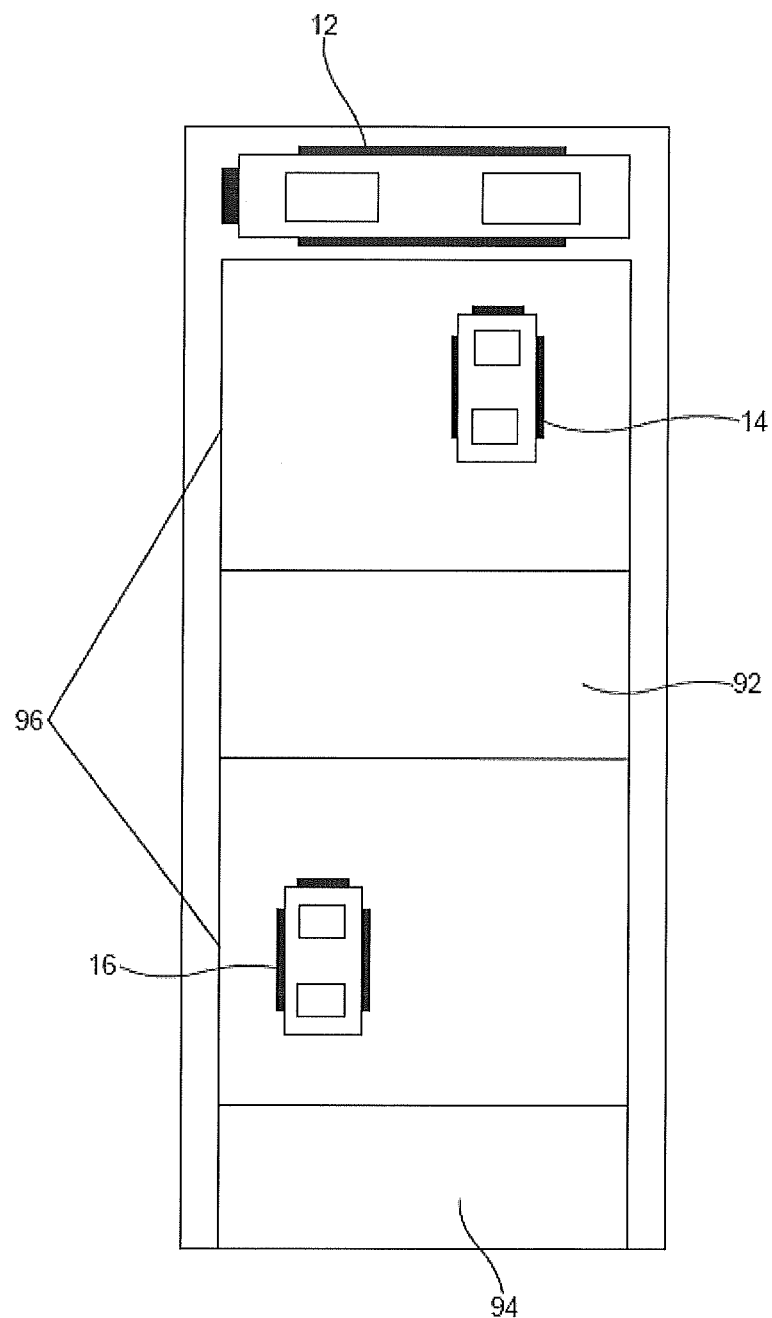
FIG. 7 shows an exemplary view of the temperature and positioning information displayed on the display device, according to an aspect of the disclosure.

The compacting machine 14 may include a "breakdown" roller which will ordinarily follow relatively closely behind the paving machine 12, such that it can compact paving material distributed by the paving machine 12 while the paving material is still relatively hot and within the optimal temperature zone (shown in FIGS. 4 and 7, as 96). Compacting with the compacting machines 14, 16, and 18 when paving material is still relatively hot and within the optimal temperature zone 96 may allow the compacting machine 14 to perform a relatively large proportion of the total compaction desired for a particular lift of paving material, as relatively hotter paving material can flow relatively readily and may be thus be readily compacted. In one aspect, the compacting machine 14 may be used primarily to compact paving material which has not yet cooled to a "tender zone" temperature range. As discussed above, the "tender zone" is a temperature range at which paving material moves or shoves in front of a drum of the advancing compacting machine 14, making attempted compaction generally undesirable. The actual temperature range at which a paving material will be within the tender zone will depend upon the particular paving material mix, and may in one aspect enter the tender zone when the temperature is within a range which may vary based on the characteristics of the paving material. Paving material may be below the tender zone when its temperature falls to within another range. Accordingly, it will typically be desirable to compact paving material with the compacting machine 14 when the temperature is within a proper range.

The compacting machine 14 may further include a receiver 28b which can receive position signals and/or control commands such as machine navigation signals, similar to the paving machine 12. The receiver 28b can include, for example, a wireless antenna and associated circuitry configured for data transmission utilizing at least one data transmission protocol, such as, for example, Wi-Fi, Bluetooth, a communication channel as defined herein, and/or the like, and/or combinations thereof.

The compact machine 14 may also include a sensor 26b mounted thereon which can sense a temperature of the paving material with which the compacting machine 14 is interacting or with which it has interacted, again similar to that of the paving machine 12. The sensor 26b may also measure ambient temperature and may be further configured to measure other data such as the composition of the paving material, its temperature when picked up from the supplier, time until delivery, the mat thickness, the ambient air temperature, underlying soil or other substrate temperature and moisture content, wind speed, solar gain, precipitation, air humidity, whether paving material is delivered directly to paving machines from haul trucks, and the like.

A transmitter 30b may also be mounted on the compacting machine 14 to transmit position data indicative of a relative or geographic position of the compacting machine 14, as well as electronic data such as temperature data acquired via the sensor 26b. In some aspects, the compacting machine 14 may include a vibratory apparatus, as will be familiar to those skilled in the paving arts.

The compacting machine 16 may include an intermediate roller which compacts paving material already compacted at least once by the compacting machine 14. The compacting machine 16 may also include a receiver 28c, a sensor 26c and a transmitter 30c, each having functions which may be similar to that of the corresponding features of the other machines described herein. It will typically be desirable to compact the paving material with the compacting machine 16 after the paving material has cooled to a temperature below the tender zone and within one of the optimal temperature zones 96. The compacting machine 16 may include an apparatus for sensing a smoothness and/or stiffness of paving material known to those skilled in the paving arts, and the transmitter 30c may be equipped to transmit data which includes smoothness and/or stiffness data for use in the system control and/or contract validation, etc., as described herein.

In the illustrated aspect, each of the compacting machines 14, 16, and 18 transmits temperature and position data which can be processed via electronic control unit 32 and used in displaying a temperature and position map via the display device 38, and may be further used in controlling machine positioning, operation, and other factors as described herein. The paving machine 12 might serve as one command center at which paving progress, machine location, and paving material temperature are monitored and data recorded. The paving operation 10 could alternatively be configured, however, such that any one of the other machines serves one or more of these functions, and in some aspects a remote command center may be employed. Accordingly, the location and distribution of the various pieces of sensing equipment, data processing and recording, map display, etc., may vary substantially from the exemplary aspect shown in FIG. 1.

The compacting machine 18 may likewise include a receiver 28d and a transmitter 30d. The compacting machine 18 may include a finish roller which may perform a final squeeze of the paving material in a particular lift, and may follow relatively closely behind the compacting machine 16. In some instances, it may be desirable to compact the paving material with the compacting machine 18 prior to its cooling below a temperature in the range of about 50° C. to about 65° C. Even where paving material is compacted to a specified relative compaction state, if compaction takes place at too low a temperature, the aggregate in the paving material may crack, creating voids which can negatively impact the long term viability of the compacted surface. To this end, the compacting machine 18 might also include a sensor 26d to verify whether the final compaction is taking place at an appropriate paving material temperature.

As discussed above, monitoring and data recording relating to the paving operation 10 may take place from a variety of locations, either onboard one of the machines 12, 14, 16, 18, 90 or at a separate command center. It is contemplated that for at least certain paving jobs, the paving operation 10 may be used with one or more control stations separate from each of the respective machines. A control station 80 may be a part of the paving operation 10, which may include a computer monitored by a paving foreman, technician, etc., and may receive signals (e.g., temperature and position data) from any or all of the machines of the paving operation 10, and may be configured to output the temperature and position data to any or all of the machines of the paving operation 10. As discussed above, the paving control system 11 may include an electronic control unit for processing electronic data generated during operation of the paving operation 10, and outputting appropriate temperature and position information, as well as storing electronic data. The control station 80 may serve as an alternative or supplemental command center where personnel can monitor paving progress, machine position, paving material temperature, and the like. To this end, the control station 80 may also include a receiver 86, an electronic controller 82, a memory 84 and a transmitter 85. The electronic controller 82 might also include a memory writing device 83 configured to record electronic data from any of the machines 12, 14, 16, 18, or 90 on memory 84.

The control station 80 may also be configured to communicate with supply machines and/or even an asphalt plant to speed up or slow down paving material production, delivery, etc., based on progress of the paving operation 10. In a related aspect, the control station 80 might be used to control supply machine traffic by directing supply machines to a particular paving machine of the paving operation 10 or by directing supply machines to a particular job site. For example, if paving at one job site or by one particular paving machine is halted for any of a variety of reasons, it may be desirable to direct supply machines to locations where paving material is needed, or where excess paving material can be best accommodated, rather than stopping the supply chain. It should be appreciated that any or all of the control and data recording aspects of the paving operation 10 might take place at the control station 80, via a laptop computer, a PDA, cell phone, tablet computer, and the like. Thus, the paving control system 11 might be located at least in part at the control station 80, rather than on one of the machines of the paving operation 10. The control station 80 may be in two-way communication with at least a portion of the machines of the paving operation 10, and also in one-way or two-way communication with machines and personnel associated with a supply chain for paving material. Additional stations (not shown), such as a quality control station and a validation station may also be used. In some instances, a quality control station may be used to record data relating to comparisons between pre-established paving specifications and actual paving parameters. The quality control station may also be used to make any necessary changes in the system operation between paving process stages, for example changes in the operation and/or speed, spacing, etc. of the compacting machines 14, 16, and 18. Quality control changes might take place via computer, or by a technician. A validation station may also be implemented at a work site to record information relating to paving specifications and paving quality, etc., for accessing by personnel other than paving contractors.

As mentioned above, the paving operation 10 may provide significant improvements over earlier paving operations with regard to providing real time temperature and position information of the paving operation, as well as gathering information relating to paving quality. This may be made possible in part by the recognition that the temperature of paving material at different stages of a paving process can be predicted and communicated, and adjustments to the paving operation can accordingly be made in real time to optimize quality where measured temperature differs from expected temperature. This differs from earlier strategies which focus on adjusting operation for future work only after determining that paving progress has not proceeded optimally. The insights set forth herein also enable establishing a plan for paving operation even prior to starting work in a manner calculated to provide the best chance of meeting specifications. It also establishes a novel standard against which data recorded during paving can be compared after a paving job is completed, for example for predictive and forensic purposes, and for refinement of planning strategies for paving in the future.

The operation of the paving operation 10 may be based on utilizing electronic data, including temperature data received via one or more of sensors 26a-d, location data of each of the machines from a satellite positioning system, and the use of a predictive positional temperature model for paving material which is recorded in or input into the computer readable memory 34. In particular, data such as actual temperature data may be utilized with data predicted by the positional temperature model. As further described herein, where sensed temperature data differs from expected or optimal data, the predictive positional temperature model may be updated and operation of the paving operation 10 can be adjusted. In one aspect, the positional temperature model may be recorded in the computer readable memory 34 of the paving control system 11, and electronic control unit 32 may use the sensed data to update the predicted positional temperature model to have more accurate predicted or optimal data. In another aspect, the positional temperature model may be, at least in part, automatically provided by sensing relevant surrounding data or downloading relevant data from another source. As discussed above, however, the model may be recorded in a computer readable memory 34 at a different location and the data processing may be carried out by a different control unit, such as at the control station 80 or on a machine of the paving operation 10 other than paving machine 12.

As used herein, the term "positional temperature model" should be understood to include any model which can be used to predict an expected paving material temperature at an identified or identifiable position at a given time. The position might be a position on a paving surface, within a supply machine, a position within the paving machine 12, or a position on a paving material mat. The position may be a position relative to one or more of the machines of the paving operation 10, or it might be a geographic position. The data may include only the temperature data of the paving material at given locations, or may consider other factors such as the composition of the paving material, its temperature when picked up from the supplier, time until delivery, the mat thickness, the ambient air temperature, underlying soil or other substrate temperature and moisture content, wind speed, solar gain, precipitation, air humidity, whether paving material is delivered directly to paving machines from haul trucks, and the like.

From the time at which paving material leaves an asphalt plant to the time at which it is worked or evaluated by the last machine of a paving operation, it will typically be cooling, albeit potentially at different rates. The mathematical representation of the rate of cooling is known as a cooling rate curve, and may be used as part of the predicted positional temperature model to display predicted position and temperature on the display device 38. Any of the many possible positions within the various machines, or anywhere on the surface being paved is a position at which the paving material's temperature might be predicted via the positional temperature model, and a sensed temperature compared therewith to update the predicted positional temperature model. Accordingly, a computer-generated prediction of a temperature of paving material at a single position would meet the intended definition of "positional temperature model." For example, a computer-based prediction of a paving material temperature of X within Y meters of a back end of screed 24 during paving could be a positional temperature model. Similarly, a computer-based prediction of a paving material temperature of Z within hopper 21 of paving machine 12 could also be a positional temperature model. Each of these examples, and many other contemplated instances, includes an identifiable position at which the paving material temperature can be predicted, compared with an actual temperature to adjust the model, and the positional temperature model updated. Computer-generated predictions of the paving material temperature at many positions would also meet the intended definition of the positional temperature model. For instance, outputs of paving material temperature from the sensors 26a-c may be associated with a position of a paving material mat relative to a position of the corresponding machine or relative to a mapped position based on an operational and positioning plan.

The use of a positional temperature model as described herein, comparison with actual temperature data to adjust the model, and an update to the positional temperature model may allow the identification of situations where paving material temperature is at or within an acceptable range of an expected temperature at a given position, as well as situations where the paving material temperature may differ from an expected or optimal temperature at a given position. The positional and temperature model can account solely for the temperature of paving material at given locations, or may also account for other factors such as the composition of the paving material, its temperature when picked up from the supplier, time until delivery, the mat thickness, the ambient air temperature, underlying soil or other substrate temperature and moisture content, wind speed, solar gain, precipitation, air humidity, whether paving material is delivered directly to paving machines from haul trucks, and the like. This information may be communicated, displayed, and leveraged to adjust operation of one or more of the machines of the paving operation 10, such as machine speed, machine spacing, conveyor speed, frequency and/or amplitude of vibrations from a vibratory compacting machine, machine path, etc. The selected machine type for compacting could also be based on this information, such as using an intermediate roller instead of a finish roller. The comparison between actual temperature data and predicted temperature data may also be recorded in computer readable memory for contract validation, predictions of road performance and durability over time, and forensic analysis of pavement failures and the like. In this manner, the disclosure addresses each of two concerns of primary importance to the paving industry, providing temperature and position information for machine operation to achieve optimum operation to meet or exceed a desired quality, and generating a reliable record that establishes whether specifications are met for a particular paving job, as well as how much a paving job might differ from specifications.

In one aspect, the positional temperature model may use a temperature decay model, predicting an expected temperature of paving material at a given position based on expected temperature decay over time. The rate at which temperature of paving material is expected to decay can vary based on a multiplicity of factors. These may include such factors as the composition of the paving material, its temperature when picked up from the supplier, time until delivery, the mat thickness, the ambient air temperature, underlying soil or other substrate temperature and moisture content, wind speed, solar gain, precipitation, air humidity, weather, whether paving material is delivered directly to paving machines from haul trucks, and the like.

In one aspect, the positional temperature model may be initialized prior to beginning work by inputting values for one or more of the foregoing parameters, and possibly others. Once the positional temperature model is initialized, an expected temperature of paving material at one or more positions within or relative to one of the paving machines of the paving operation 10 or at a position on the mat may be predicted based on the model. In one example, the positional temperature model might be used to predict a paving material temperature immediately behind each of the machines 12, 14, 16, and 18. A predicted temperature map of a work area, including paving material temperatures at each of the selected positions behind the machines 12, 14, 16, and 18 may be generated, for example via the display device 38. Once paving begins, temperatures at each of the selected positions may be sensed via the sensors 26a-d, and a comparison may be made by the electronic control unit 32 or display device 38 between sensed and predicted temperatures, and the positional temperature model. The resulting data may be updated, simplified, and displayed by the display device 38.

In one aspect, the electronic control unit 32 may be configured to generate a signal which is based on comparing temperature data received via one or more of the temperature sensors 26a-d with a temperature predicted by the positional temperature model for the positions scanned with the temperature sensors 26a-d. The signal may include a display signal to the display device 38 which can indicate to personnel viewing a map displayed on the display device 38 that a difference between sensed temperature and predicted temperature exists. The signal may also include a machine navigation signal which directs an operator on one of the machines 12, 14, 16, and 18 to start, stop, speed up, slow down, change direction, repeat a pass across a particular area of the mat, etc. In one specific aspect, the signals might be transmitted directing two or more of the machines 12, 14, 16, and 18 to adjust the relative spacing between them to avoid compacting an area of the mat which is within a predefined temperature range such as the tender zone, or to ensure that a particular area of the mat is compacted while in a predefined temperature range. Where appropriate, a machine navigation signal could be broadcast via transmitter 30a. The signal might also include a control signal to propulsion elements of the paving machine 12 to adjust speed and potentially also to the conveyor system 23 to adjust speed to accommodate changes in speed of the paving machine 12. In still other instances, the signals could be transmitted to the supply machine 90 to indicate an expected change in demand for paving material, to an asphalt plant to request a change in output, etc.

The signals generated in response to comparing the sensed temperature data with predicted positional temperature model data could also simply be recorded in memory such as the computer readable memory 34. Such signals might include a signal indicating that specifications are met, or a signal indicating that specifications are not met. For example, the electronic control unit 32 or display device 38 might create a log of temperature data for a position directly behind the paving machine 12, demonstrating that paving material at that selected position was consistently within a specified temperature range throughout an entire paving operation for contract validation purposes. In some aspects, temperature mapping data for an entire work site, for a plurality of lifts of paving material, including machine position data, may be recorded in computer readable memory 34, establishing an entire temperature history for a paving job. Model comparison data, as described herein, which corresponds with the temperature data may also be recorded. The sensed paving material stiffness and a paving material smoothness may also be recorded. In certain versions, the disclosure can allow a paving contractor or auditor to establish exactly what temperature each portion of the mat was at during any given time, what the model-predicted temperature for that portion of the mat was and where each machine of the paving operation 10 was at any given time, enabling a detailed analysis of the paving job from start to finish.

As mentioned above, the positional temperature model may also be used in planning a particular paving job. For example, in some instances the optimum spacing and/or speed of machines of the paving operation 10 may vary based on the rate of cooling of paving material. Where paving material is predicted by the model to cool relatively rapidly, for example because of low ambient temperatures, it may be desirable for the machines 12, 14, 16, and 18 to travel faster and relatively closer together to enable compaction to take place prior to the paving material cooling below a specified temperature. Where paving material is predicted by the model to cool relatively more slowly, for example because of a high ambient temperature, it may be desirable for the machines 12, 14, 16, and 18 to travel more slowly and/or relatively further apart.

While the conditions upon beginning a paving job can be used to initialize the positional temperature model and establish a plan relative to machine positioning, machine speed, etc., the conditions may change. For example, the composition of the paving material, its temperature when picked up from the supplier, time until delivery, the mat thickness, the ambient air temperature, underlying soil or other substrate temperature and moisture content, wind speed, solar gain, precipitation, air humidity, whether paving material is delivered directly to paving machines from haul trucks, etc., may all change throughout the course of work day, affecting the validity and/or accuracy of a positional temperature model. In some instances, the positional temperature model may be updated to account for changing conditions, by inputting updated model parameters or sensing them automatically with the sensors 26a-d. The plan may therefore be changed in accordance with the updated model, and the paving operation 10 may be operated according to the updated plan by outputting appropriate positional temperature information, navigation signals, speed signals, etc. to adjust operation.

Figure 2:
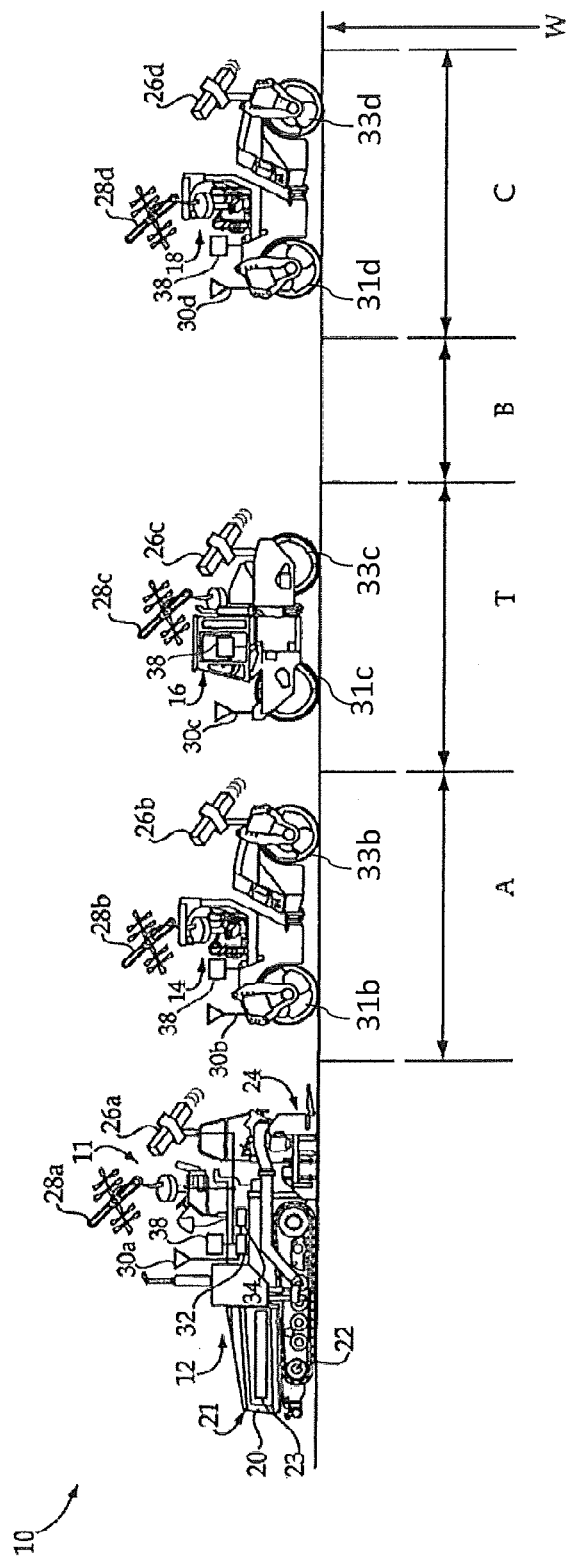
FIG. 2 shows a system in which a paving machine lays a paving material on a surface to be compacted by multiple compacting machines, one of which enters a tender zone.

Turning now to FIG. 2, there are shown the machines 12, 14, 16, and 18 of the paving operation 10 in relation to a work surface W. The paving machine 12 has distributed a mat of paving material on work surface W, and each of the compacting machines 14, 16, and 18 is following behind paving machine 12, successively compacting the mat. Compacting machine 14 may be following relatively closely behind the paving machine 12, such that it is compacting a portion of the mat, zone A in FIG. 2, which is at a temperature above a tender zone 92 temperature and in an optimal temperature zone 96 (shown in FIG. 7). A portion of the mat which is behind the compacting machine 14 may actually be in the tender zone 92, represented, by zone T in FIG. 2. In this regard, without any information, the compacting machine 16 may be following behind the paving machine 12, partially within the tender zone 92 or approaching the tender zone 92. This results in undesirable compacting.

On the other hand, implementing the paving operation 10 using the disclosed device and/or process may avoid compacting on the portion of the mat within the tender zone 92.

Figure 3:
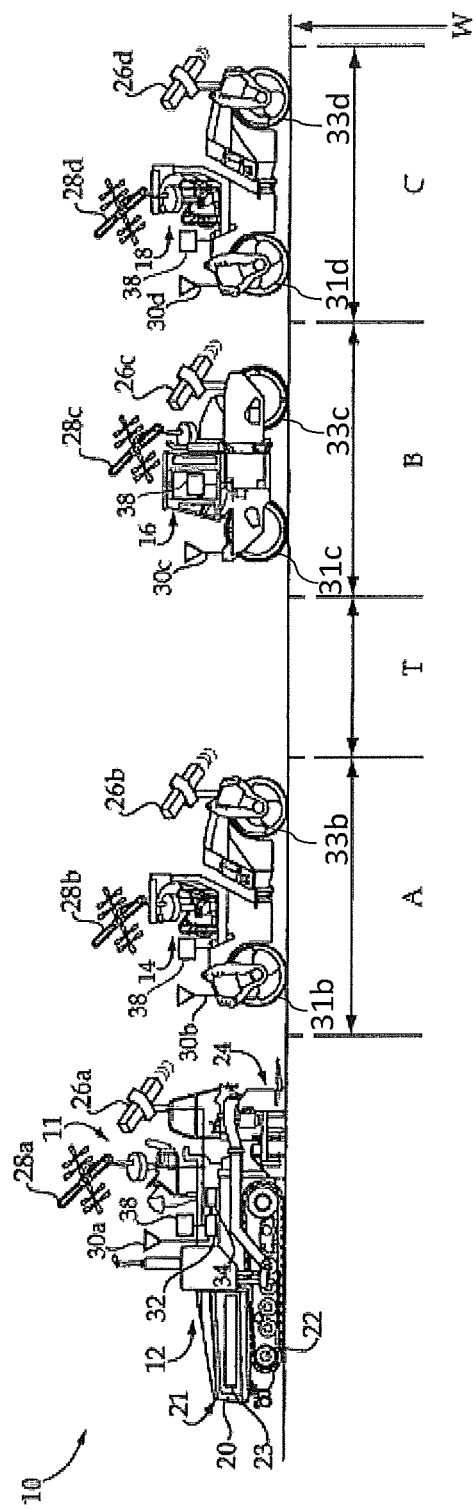
FIG. 3 shows a system in which a paving machine lays a paving material on a surface to be compacted by multiple compacting machines avoiding a tender zone, according to an aspect of the disclosure.

As mentioned above, the machines of the paving operation 10 may be operating at a specified speed, or with a specified spacing, etc., which is based on an expected temperature decay of paving material. In other words, the paving operation 10 will typically be proceeding in some sort of planned manner which is based on the expected temperatures of paving material at different stages in the paving process, as predicted by the positional temperature model. The machine 16 may be further spaced behind the compacting machine 14 as shown in FIG. 3 to allow the paving material time to cool to below the tender zone, and may compact a relatively cooler portion of the mat, shown as zone B in FIG. 3. Zone B may be within an optimal temperature zone 96. The compacting machine 18 may be positioned behind the machine 16 to compact the still cooler portion of the mat, zone C, which has not yet cooled below a minimum specified temperature. If, for example, the compacting machine 18 is following the compacting machine 16 by a distance that is far enough behind the compacting machine 16 that the compacting machine 18 is not going to reach zone C until zone C becomes too cold for compacting, the spacing between the compacting machine 16 and the compacting machine 18 may be adjusted so that the compacting machine 18 may compact zone C while zone C is still within an optimal temperature zone 96.

A map of a particular portion of a work area may be displayed via the display device 38 of the paving machine 12, or a different display at a different location. Each of the machines 12, 14, 16, and 18 may also be represented on the map (as shown in FIG. 4 and FIG. 7) such that an operator or foreman can view the temperature of paving material in relation to the position of the various machines, based on position signals from each of the machines Thus, FIG. 3 may be one implementation of such a map, wherein paving material temperature on work surface W and machine type and location is displayed on the display device 38. A different display strategy, such as a two-dimensional bird's eye view, illustrating paving material in different colors corresponding to different temperatures might also be used such as shown in FIGS. 4 and 7.

The machines 12, 14, 16, 18 may be scanning temperature of paving material continuously or at least periodically as the paving process progresses. Any suitable strategy for sensing paving material temperature may be used. In one aspect, sensors 26a-d may be rotated to sweep back and forth, scanning the regions of the mat directly behind the corresponding machine across a width of the mat approximately identical to the machine's width. Since the machines 12, 14, 16, and 18 will typically be traveling forward along a work surface, the area that is actually scanned may include a zigzagging path back and forth behind the corresponding machine, including substantially less than the entire portion of the mat with which the corresponding machine interacts. For purposes of processing the temperature data, as well as displaying the temperature data to an operator or foreman, etc., and storing the temperature data, the work area may be divided into segments perpendicular to the machine path having a width equal to the machine width. Each of the segments may have its temperature determined based on the points of the scanning path which intersect the subject segment. In other words, while the zigzagging path will only actually scan a relatively small portion of the mat, the temperature of an entire segment of a mat perpendicular to the machine's path which has just been worked can be estimated by the relatively small number of points, potentially only one, of the zigzagging path which actually intersect each segment. One advantage of this strategy is that a relatively simple and inexpensive temperature sensor may be used, such as a non-optical sensor, and the total amount of data may be substantially less than that required if attempting to record temperature information for an entire work area.

It may also be desirable in some instances to capture thermal images of an entire work surface by scanning numerous locations of a mat with which a machine has interacted or is about to interact, then associating each of the locations with position data. For example, a thermal camera or the like, or multiple point sensors, could initially produce data corresponding to the two-dimensional surface of the mat. Next, each data point, for example, each pixel of a thermal image, could be associated with a positioning system, such as a satellite positioning system. A computer, such as the electronic control unit 32, may then store data from the entire area as temperature data with the corresponding position data. Each data set, of temperature data and position data, may also be associated with time data, such that each sensed area of a mat could have a temperature coordinate, a position coordinate and a time coordinate. Where multiple lifts of paving material are used, a lift number coordinate could also be used. The data sets could then be retrieved to allow a technician, etc. to later view displays of a complete thermal history of a paved work area. The data sets could also be displayed on the display device 38 for analysis or processing.

It will further be recalled that sensed paving material temperature may be compared with paving material temperature predicted by the positional temperature model and displayed on the display device 38. The comparison may take place, for example, with the electronic control unit 32, which will typically output signals corresponding to a difference between the positional temperature model and temperature data gathered via one or more of the sensors 26*a-d*. During the paving operation 10, situations may develop in which one or more of the machines of the paving operation 10 is working with paving material which is not at an optimum temperature for the particular type of work, or is not within an optimal temperature zone 96. For example, by sensing paving material temperature, machine position, etc., it may be discovered that one of compacting machines 14, 16, and 18 is attempting to compact paving material which is in the tender zone (92 in FIG. 4) or a cold zone (94 in FIG. 4), or is progressing toward paving material which is in the tender zone 92 or cold zone 94. If one of the compacting machines 14, 16, or 18 is within the tender zone 92 or cold zone 94, the electronic control unit 32 may send a message to the display device 38 and to the compacting machines 14, 16, and 18 indicating this. If one of the compacting machines 14, 16, or 18 is approaching a tender zone 92 or cold zone 94, the electronic control unit 32 may send a message to the display device 38 and to the compacting machines 14, 16, and 18 indicating the time remaining before the compacting machine 14, 16, or 18 reaches the tender zone 92 or cold zone 94.

Referring to FIG. 3, there is shown an exemplary representation of the paving operation 10, wherein compacting machine 16 is working paving material which is determined to be in zone T, the tender zone 92 for the particular paving material mix. Similar to the FIG. 2 illustration, it should be appreciated that an operator, foreman, etc. might view a map similar to FIG. 3, but could also view any other suitable graphical representation of the relevant portion of a work area, and the machine(s) 12, 14, 16, and 18 within that area.

When it is determined that one or more of the machines 12, 14, 16, and 18 of the paving operation 10 is working with or is about to work with paving material that is too hot or too cool, a control signal to the machines 12, 14, 16, and 18 may be output via the electronic control unit 32, via the transmitter 30*a*, and/or to the display device 38, for example. In one aspect, the control signal could include a machine navigation signal which directs the subject machine, in the illustrated case the compacting machine 16, to stop, reduce its speed, maintain a particular spacing from the compacting machine 14, or to take a variety of other actions. The case where the compacting machine 16 is compacting paving material which is within the tender zone 92 might occur, for example, where the compacting machine 16 is traveling above a specified speed and begins to get too close to the compacting machine 14 such that the paving material does not have sufficient time to cool after being compacted with the compacting machine 14. Such a situation might also occur where environmental conditions change and the paving material cools more slowly than expected, for instance where ambient temperature rises significantly over the course of a work day. The communication and changing of paving operations may also be changed manually upon the determination that one or more of the machines of the paving operation 10 is working with or is about to work with paving material that is too hot or too cool, and that determination may be based on what is shown on the display device 38.

While avoiding the tender zone 92 of paving material is contemplated to be one practical implementation of the disclosure, numerous other instances exist where the paving operation 10 can be controlled to accommodate paving material temperatures which are different from expected temperatures. For instance, where paving material temperature immediately behind the paving machine 12 is determined to be too cool, the electronic control unit 32 may output control signals to the conveyor system 23 to increase its rate of supplying paving material to the screed 24, and may also output control signals to a propulsion system (not shown) of the paving machine 12 to increase the speed of operation of ground engaging elements 22 to increase machine travel speed. Simultaneously, machine speed signals could be output to other machines of the paving operation 10 to accommodate an increased paving speed. Signals may also be sent to supply machine, or even an asphalt plant, to speed up the rate at which paving material is supplied to the paving operation 10.

Referring to FIGS. 1 and 4, the electronic control unit 32 may communicate with the display device 38 on an operator interface that may display a paving machine 12, compacting machines 14, 16, and 18, the tender zone 92 of the asphalt, the zone in which the asphalt temperature is too cold (e.g., the "cold zone" 94), the optimal temperature zones 96 in which to compact the asphalt, and the like. The display device 38 may display information and images based on data collected by or input into the electronic control unit 32. The electronic control unit 32 may also communicate with the paving machine and the compacting machines 14, 16, and 18 working on the same or different sections of road. Each paving machine 12 may be equipped with a display device 38 to communicate with each compacting machine 14, 16, and 18 on the same project or stretch of road. In another aspect, each paving machine 12 may be paired with one or more compacting machines 14, 16, and 18 in a master-slave relationship controlled by the electronic control unit 32 and the display device 38. In yet another aspect, one paving machine 12 may control all compacting machines 14, 16, and 18 on a project with the electronic control unit 32 and the display device 38. In still another aspect, each paving machine 12 and compacting machine 14, 16, and 18 may have a display device 38.

The display device 38 may display the position of one or more paving machines 12 and the compacting machines 14, 16, and 18. The paving machine 12 may be accompanied by one or more compacting machines 14, 16, and 18. Because of the varying temperature of paving material to be paved, the display device 38 may display the temperatures of various parts of the surface. In addition, the display device 38 may determine and display zones in which the paving material is too hot or cold to be compacted. In one aspect, the display device 38 may display a tender zone 92 that represents a temperature or temperature range in which no paving material should be compacted. In another aspect, the display device 38 may determine and display a temperature or temperature range in which the paving material is too cold to compact 94. The tender zone 92 or zone in which the paving material is too cold 94 to compact may be displayed by the display device 38 so that the operator of a paving machine or compacting machine 14 may adjust operations to pave or compact. The tender zone 92 and cold zone 94 may be displayed on the display device 38 by showing colored areas marking the zones in which the paving material is not suitable for compacting. The colored zones showing the beginning and end of each zone may be the same color or different colors. While it may be preferred not to show color gradients to represent the proximity of any machines to sub-optimal paving zones, other aspects may display such gradients on the display device 38.

The electronic control unit 32 and display device 38 may also communicate with paving machines 12 and compacting machines 14, 16, and 18 to automatically control operation of the machines so that they cannot pave or compact when the paving material is not within the optimal compacting temperature range or ranges.

In another aspect, the electronic control unit 32 may determine an optimal temperature zone 96 in which compacting may occur. This determination can be accomplished using an algorithm based on the cooling rate curve of the paving material. The electronic control unit 32 may also determine multiple optimal temperature zones 96 and may display them on the display device 38 relative to the paving machine 12 and the compacting machines 14, 16, and 18. If the electronic control unit 32 determines that the temperature of the paving material is within an optimal temperature zone 96 using the temperature and position data and the predicted positional temperature model, the electronic control unit 32 or display device 38 may communicate to the paving machine 12 and to the compacting machines 14 that they may perform paving and compacting processes. In another aspect, the electronic control unit 32 may remotely control the operation of the paving machine 12 and the compacting machines 14, 16, and 18 in order to prevent paving and compacting operations when the electronic control unit 32 determines that the temperature of the paving material is not within an optimal temperature zone 96 using the temperature and position data and the predicted positional temperature model. Referring to FIG. 4, the display device 38 may be configured to display the optimal temperature zones 96 either with colors or no colors to differentiate them on the display device 38 from the tender zones 92 and cold zones 94.

It may also be desirable to specify spacing between the compacting machines 14, 16, and 18 and the paving machine 12 to produce an optimally smooth surface. For example, if the compacting machine 14 is too close to the paving machine 12, it can encounter paving material of the mat which has not yet cooled to an appropriate temperature for compacting. If the compacting machine 14 is traveling too far behind the paving machine 12, it may be working with paving material that has cooled too much for optimal compacting. In either case, working of paving material that is not at an optimum temperature can result in improper compaction, immediately or eventually leading to a pavement having suboptimal smoothness. In a related vein, the compacting machine 14 travel speed may be specified by the operator interface 70 to maintain a specified spacing between the compacting machine 14 and the paving machine 12 based on the predicted positional temperature model. The compacting machine 14 travel speed may be set by an operational and positional plan provided to the electronic control unit 32 and/or display device 38 and available for display on the display device 38. It may be desirable to adjust the operation and position of the compacting machines 14, 16, and 18 based on the position of the compacting machines 14, 16, and 18 and the temperature of paving material on the surface being paved based on the predicted positional temperature model.

In one aspect, the electronic control unit 32 or display device 38 may determine that a compacting machine 14 may be approaching paving material that is not within the optimal temperature zone 96 and is thus not suitable for compacting based on the predicted positional temperature model. The electronic control unit 32 or display device 38 may communicate to the compacting machine 14 and the paving machine 12 to adjust spacing between the compacting machine 14 and the paving machine 12 so that the compacting machine 14 does not compact paving material outside of the optimal temperature zone 96. The communication between the electronic control unit 32, the display device 38, the compacting machine 14, and the paving machine 12 may be executed by communication via the electronic control unit 32 or display device 38, the operator interface 70, the transmitters 30*a-b*, and the receivers 28*a-b*. The compacting machine 14, paving machine 12, or the operator of the compacting machine 14 and/or paving machine 12 may, in response, also lockout operations to prevent compacting on the paving material that is outside of the optimal temperature zone 96.

Figure 5:
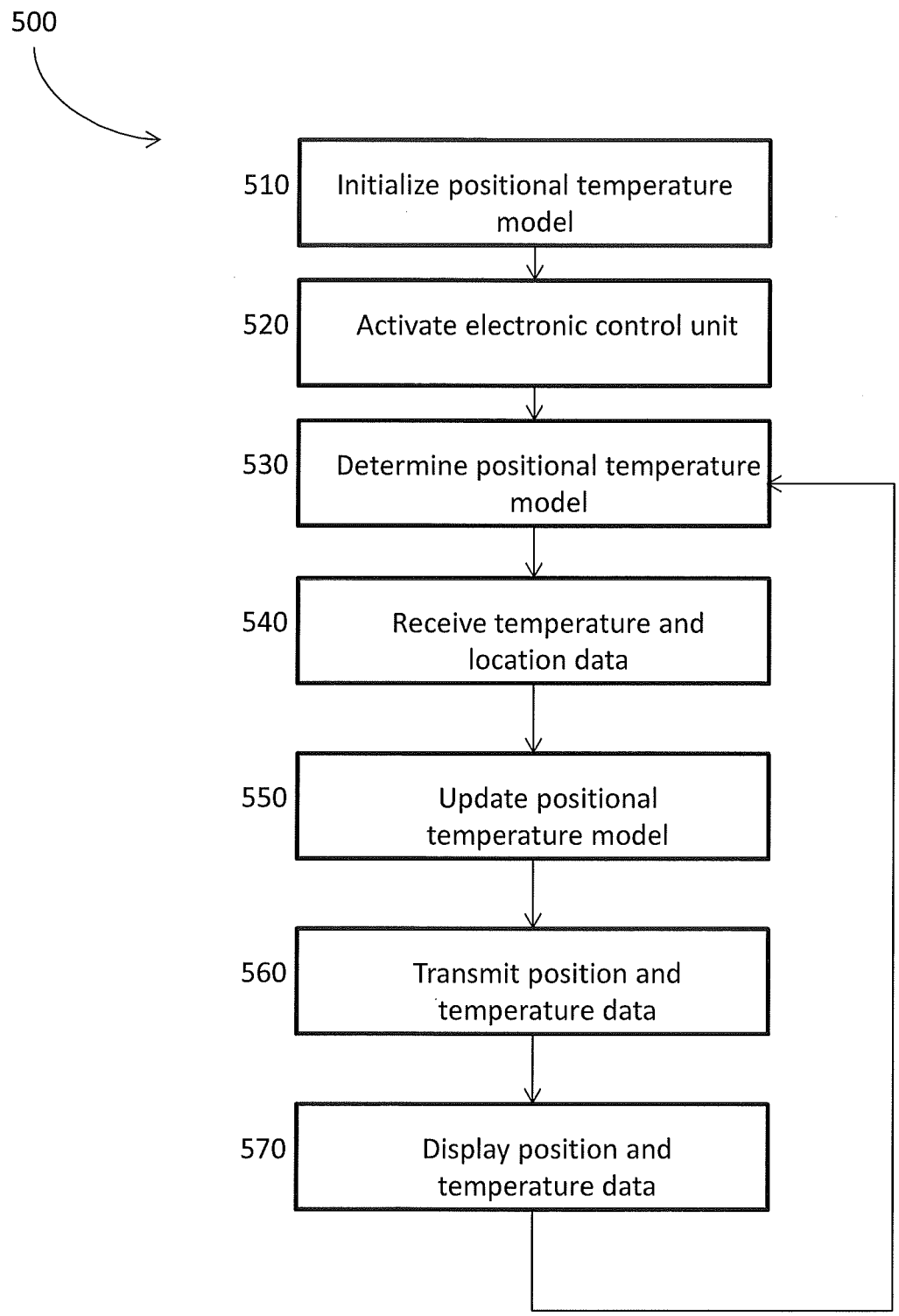
FIG. 5 details a process of displaying and communicating the temperature and position data relating to compacting paving material in conjunction with a positional temperature model, according to an aspect of the disclosure.

Referring now also to FIG. 5, there is shown a flowchart for the method 500 illustrating an exemplary display process according to the disclosure used with the paving operation 10. The process of method 500 starts at step 510 by initializing the positional temperature model. Initialization of the positional temperature model may include inputting values for one or more model parameters which allow a prediction of paving material temperature at any of numerous possible positions within or relative to machines of the paving operation 10, or geographic positions. Factors such as the composition of the paving material, its temperature when picked up from the supplier, time until delivery, the mat thickness, the ambient air temperature, underlying soil or other substrate temperature and moisture content, wind speed, solar gain, precipitation, air humidity, weather, whether paving material is delivered directly to paving machines from haul trucks, and the like may all be input to the positional temperature model.

The process moves to step 520 by activating the electronic control unit 32. Activation may include activating the sensor 26*a*, the receiver 28*a*, the transmitter 30*a*, and the display device 38. Activation may include inputting into the electronic control unit 32 and/or the display device 38 the operational and positional plans, temperature data and models, and the like. Next, at step 530, the positional and temperature model is determined. The model may be a relatively simple one that indicates and displays the machines 12, 14, 16, and 18 and the various temperature zones, such as the tender zone 92. The model may be one wherein spacing between the machines 12, 14, 16, and 18 to avoid the tender zone 92 is displayed. Relatively more sophisticated plans may also be used, wherein a plurality of different parameters such as machine speed, vibratory amplitude and frequency for vibratory apparatuses of one or more of the compacting machines, screed heating, etc., may be determined.

It should thus be understood that "machine positioning" is but one example of the many different factors which might be determined based on the positional temperature model. In still other aspects, rather than initializing the model each time a particular job is begun, a one-size fits all positional temperature model might be used, developed empirically or via computer simulation, for example. Temperature and positional plan data corresponding to the established plan may be recorded in memory 34, memory 84, etc. by the appropriate electronic control unit 32 and/or 82 via a memory writing device such as memory writing device 83. In one aspect, establishing of the plan may be performed by the subject electronic control unit 32 which may calculate the appropriate machine operating parameters such as speed, positioning, etc. which correspond with the plan, and are ultimately based on the positional temperature model. A one-size fits all plan based on a one-size fits all positional temperature model might also be used. In still other aspects, the plan might be established manually by operators, foremen, etc.

At step 540, appropriate positional and temperature data may be transmitted and received to commence paving. The positional and temperature data may include the temperature of the paving material at given locations, the locations of compactors 14, 16, and 18, the composition of the paving material, its temperature when picked up from the supplier, time until delivery, the mat thickness, the ambient air temperature, underlying soil or other substrate temperature and moisture content, wind speed, solar gain, precipitation, air humidity, weather, whether paving material is delivered directly to paving machines from haul trucks, and the like. After receiving temperature and location data, the process may proceed to step 550 wherein the positional and temperature model may be updated based on the data received at step 540. As discussed above, temperature data might include temperature data at positions of a paving material mat relative to one of the machines 12, 14, 16, and 18 of the paving operation 10, mapped locations of a work area, temperature data for paving material, etc.

If a paving material temperature is within the optimal temperature zone 96, the electronic control unit 32 may transmit 560 to the compacting machines 14, 16, and 18 that the compacting machine 14, 16, and 18 may compact the paving material. If, however, the comparison shows that the temperature is not within the optimal temperature zone 96, the electronic control unit 32 may transmit 560 to the compacting machine 14, 16, and 18 that the compacting machine 14, 16, and 18 should not compact the paving material. The electronic control unit 32 or display device 38 may also transmit 560 positional and temperature data to other machines. At step 570, the position and temperature data may be displayed on one or more display devices 38 on one or more machines To display the data, the display device 38 may convert received data and execute algorithms based on predictive models, cooling curves, etc. An exemplary output of the display device is shown in FIG. 4. The method 500 may continually repeat steps 530-570, and all steps may be performed by one or more processors on the operator interface 70, the display device 38, and/or the electronic control unit 32.

Figure 6:
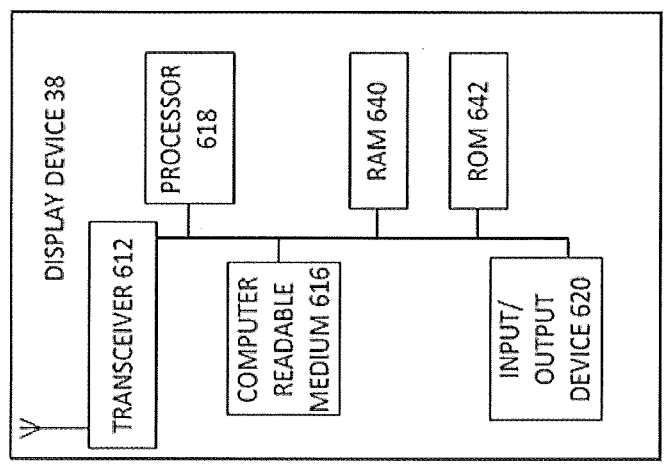
FIG. 6 shows a detailed view of the components of the display device, according to an aspect of the disclosure.

FIG. 6 shows an aspect of the display device 38. The display device 38 may include a transceiver 612, a computer readable medium 616, a processor 618, an output device 620, a random access memory 640, a read only memory 642, and an input/output device 620. The transceiver 612 may be configured to communicate with the paving machine 12 or the compacting machines 14, 16, and 18 to communicate the position and temperature information on a communication channel as defined herein. The processor 618 may collect temperature and positioning data and may take the temperature and positioning data and apply it to a temperature positioning model to predict temperature and positioning data and configure the position and temperature data for display on the display device 38. The position and temperature data may be translated by the processor 618 for simplified display on the display device. The position and temperature data may be limited to the temperature of paving material at a given location or may include additional factors such as the composition of the paving material, its temperature when picked up from the supplier, time until delivery, the mat thickness, the ambient air temperature, underlying soil or other substrate temperature and moisture content, wind speed, solar gain, precipitation, air humidity, weather, whether paving material is delivered directly to paving machines from haul trucks, and the like.

The random access memory and read only memory 642 may be used to store scripts associated with the configuration of the display device 38 and to store positional temperature data and models. The input/output device 620 may communicate to the electronic control unit 32 and the operator interface 70 to transfer data and to control operations.

FIG. 7 shows a more detailed view of the temperature and positional information that may be displayed on the display device 38. In one example, the data may be converted onto the display device 38 as a map. The temperature and positional plan may show the location of the paving machine 12 and of the compacting machines 14, 16, and 18 relative to each other and to various temperature zones of a surface being paved. The optimal temperature range 96 may be displayed along with a tender zone 92 and a cold zone 94. Each temperature zone may be noted by text showing the temperature of the zones or whether the zones are suitable for paving. The temperature zones may also be colored in a way to show that the zones are too hot or cold for paving (e.g., a red zone for the tender zone 92 and a blue zone for a cold zone 94).

INDUSTRIAL APPLICABILITY

Turning to FIG. 1, a paving machine 12 may be followed by one or more compacting machines 14, 16, and 18. As paving material is placed by the paving machine 12, the compacting machines 14, 16, and 18 may compact paving material placed by the paving machine 12. The temperature of the paving material may vary based on a variety of factors. Depending upon the particular mix of paving material, it may have a temperature range known in the art as the "tender zone" 92 where attempted compacting is not desired. When paving material is in the tender zone 92 it is prone to shoving and there may be a "wave" in front of the compactor drum. It is well known in the paving arts that successful compaction may take place when the paving material temperature is either above the tender zone 92 or below the tender zone 92, but not within the tender zone 92. Ideally, breakdown rollers, mentioned above, follow the paving machine closely enough that they compact paving material prior to its cooling to the tender zone 92. Intermediate rollers typically follow sufficiently far behind the breakdown roller that the paving material has cooled below the tender zone 92 by the time the intermediate roller reaches a particular stretch of paving material. It is also typically desirable to employ the finish roller prior to paving material cooling to a point at which it becomes too hard.

The device and method of displaying and communicating temperature of the paving material may facilitate communication of position and temperature data between machines and operators so that the operators and machines may execute the compaction processes only when the temperature of the paving material is suitable. This can lead to a more successful and efficient paving and compaction process.

Referring to FIGS. 1 and 4, the temperature sensor 26a may scan paving material temperature deposited on a work surface. Meanwhile, a receiver 28a may receive position data of other machines from transmitters 30b, 30c, and 30d. The sensor 26a, receiver 28a, and transmitter 30a may be coupled with an electronic control unit 32. Temperature and position data may be processed by electronic control unit 32, compared with operational and positional plans applied to the positional temperature model, the positional temperature model updated, analyzed, and converted for display, communicated to an operator interface 70 with a display device 38, and displayed on the display device 38.

Temperature and position data, based at least in part on the positional temperature model, may be displayed on the display device 38 so that an operator may determine what, if any, operational functions should be used, modified, or locked out. An operator may determine, based on the temperature and position data displayed on the display device 38 from the electronic control unit 32, that the spacing between a paving machine 12 and any compacting machines 14, 16, and 18 should be adjusted so that no compacting may be performed when the temperature of the paving material is outside of an optimal temperature zone 96.

Alternatively, the electronic control unit 32 may determine what, if any, operational functions should be used, modified, or locked out. The electronic control unit 32 may communicate to the operator interface 70 on the same machine or, via the transmitter 30, to another machine. The electronic control unit 32 may thus communicate with and control the machine on which it sits or may remotely communicate with and control other machines. This operational control may be based on whether or not temperature and position data based at least in part on the positional temperature model suggest that the paving material used is within an optimal temperature zone 96.

It will be appreciated that the foregoing description provides examples of the disclosed system and technique. However, it is contemplated that other implementations of the disclosure may differ in detail from the foregoing examples. All references to the disclosure or examples thereof are intended to reference the particular example being discussed at that point and are not intended to imply any limitation as to the scope of the disclosure more generally. All language of distinction and disparagement with respect to certain features is intended to indicate a lack of preference for those features, but not to exclude such from the scope of the disclosure entirely unless otherwise indicated.

According to an example, a device and/or system may estimate its location based, at least in part, on signals received from space vehicles (SVs). In particular, such a device and/or system may obtain pseudorange measurements including approximations of distances between associated SVs and a navigation satellite receiver. In a particular example, such a pseudorange may be determined at a receiver that is capable of processing signals from one or more SVs as part of a Satellite Positioning System (SPS). Such an SPS may include, for example, a Global Positioning System (GPS), Galileo, Glonass, to name a few, or any SPS developed in the future. To determine its location, a satellite navigation receiver may obtain pseudorange measurements to three or more satellites as well as their positions at time of transmitting. Knowing the SVs' orbital parameters, these positions can be calculated for any point in time. A pseudorange measurement may then be determined based, at least in part, on the time a signal travels from an SV to the receiver, multiplied by the speed of light. While techniques described herein may be provided as implementations of location determination in GPS and/or Galileo types of SPS as specific illustrations according to particular examples, it should be understood that these techniques may also apply to other types of SPS, and that claimed subject matter is not limited in this respect.

The disclosure may be implemented in any type of computing devices, such as, e.g., a desktop computer, personal computer, a laptop/mobile computer, a personal data assistant (PDA), a mobile phone, a tablet computer, cloud computing device, and the like, with wired/wireless communications capabilities via the communication channels.

Further in accordance with various aspects of the disclosure, the methods described herein are intended for operation with dedicated hardware implementations including, but not limited to, PCs, PDAs, semiconductors, application specific integrated circuits (ASIC), programmable logic arrays, cloud computing devices, and other hardware devices constructed to implement the methods described herein.

It should also be noted that the software implementations of the disclosure as described herein are optionally stored on a tangible storage medium, such as: a magnetic medium such as a disk or tape; a magneto-optical or optical medium such as a disk; or a solid state medium such as a memory card or other package that houses one or more read-only (non-volatile) memories, random access memories, or other re-writable (volatile) memories. A digital file attachment to email or other self-contained information archive or set of archives is considered a distribution medium equivalent to a tangible storage medium. Accordingly, the disclosure is considered to include a tangible storage medium or distribution medium, as listed herein and including art-recognized equivalents and successor media, in which the software implementations herein are stored.

The disclosure may include communication channels that may be any type of wired or wireless electronic communications network, such as, e.g., a wired/wireless local area network (LAN), a wired/wireless personal area network (PAN), a wired/wireless home area network (HAN), a wired/wireless wide area network (WAN), a campus network, a metropolitan network, an enterprise private network, a virtual private network (VPN), an internetwork, a backbone network (BBN), a global area network (GAN), the Internet, an intranet, an extranet, an overlay network, a cellular telephone network, a Personal Communications Service (PCS), using known protocols such as the Global System for Mobile Communications (GSM), CDMA (Code-Division Multiple Access), Long Term Evolution (LTE), W-CDMA (Wideband Code-Division Multiple Access), Wireless Fidelity (Wi-Fi), Bluetooth, and/or the like, and/or a combination of two or more thereof.

Additionally, the various aspects of the disclosure may be implemented in a non-generic computer implementation. Moreover, the various aspects of the disclosure set forth herein improve the functioning of the device and method as is apparent from the disclosure hereof. Furthermore, the various aspects of the disclosure involve computer hardware that it specifically programmed to solve the complex problem addressed by the disclosure. Accordingly, the various aspects of the disclosure improve the functioning of the device and method overall in their specific implementation to perform the process set forth by the disclosure and as defined by the claims.

Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context.

We claim:

1. An operator interface, comprising:
   a transceiver configured to receive temperature and position information of a portion of a paving material from one or more sensors;
   a processor in communication with the transceiver and configured to determine a plurality of predicted temperatures associated with a plurality of positions of the paving material based on the temperature and position information and a temperature and positional model that is defined by a cooling curve; and
   a display device in communication with the processor and configured to display a graphical user interface configured to receive operator input, convert the plurality of predicted temperatures of the paving material at the plurality of positions of the paving material into a map within the graphical user interface displaying a plurality of different temperature zones spatially positioned relative to at least one machine, and identify at least one operational function of the at least one machine to be locked out in at least one of the temperature zones.

2. The operator interface of claim 1, wherein the transceiver is configured to receive the temperature and position information of the portion of the paving material from one or more temperature sensors that are mounted on the at least one machine.

3. The operator interface of claim 1, wherein the transceiver is configured to receive the temperature information from a temperature sensor configured to determine a temperature of the paving material at a particular location, and receive the position information from a position sensor configured to determine a position of the particular location.

4. The operator interface of claim 1, further comprising a memory in communication with the processor and configured to retrievably store one or more temperature and positional models accessible by the processor, each of the temperature and positional models being defined at least partially based on a cooling curve associated with the paving material.

5. The operator interface of claim 4, wherein the processor is configured to retrieve the temperature and positional model from the memory.

6. The operator interface of claim 1, further comprising one or more input devices configured to receive operator input, the display device being configured to adjust the map displayed within the graphical user interface in response to the operator input.

7. The operator interface of claim 1, wherein the plurality of different temperature zones include a tender zone, a compaction zone, and a cold zone.

8. The operator interface of claim 7, wherein the tender zone is represented on the display by a first color filling the space between a starting location and an end location of the tender zone, and wherein the cold zone is represented on the display by a second color filling the space between the starting location and the end location of the cold zone.

9. The operator interface of claim 7, wherein the temperature and positional model is based in part on one or more of an ambient temperature, a wind speed, weather, humidity, paving material type, and a moisture level.

10. The operator interface of claim 7, wherein the display device is configured to identify that a compacting operational function is locked out in the tender zone and the cold zone.

11. A method of determining and displaying predicted temperatures of paving material on an operator interface, the method comprising:
    receiving, at a transceiver, temperature and position information of a portion of the paving material from one or more sensors;
    determining, at a processor, at least one temperature and positional model based on a cooling curve;
    determining, at the processor, a plurality of predicted temperatures of the paving material each associated with a plurality of positions of the paving material based on the temperature and positional model and the temperature and position information;
    displaying, at a display device, a graphical user interface configured to receive operator input;
    converting, at the display device, the plurality of predicted temperatures of the paving material at the plurality of positions of the paving material into a map within the graphical user interface displaying a plurality of different temperature zones spatially positioned relative to at least one machine; and
    identifying, at the display device, at least one operational function of the at least one machine to be locked out in at least one of the temperature zones.

12. The method of claim 11, wherein the temperature and position information of the portion of the paving material is received from one or more temperature sensors that are mounted on the at least one machine.

13. The method of claim 11, wherein the temperature information is received from a temperature sensor configured to determine a temperature of paving material at a particular location, and the position information is received from a position sensor configured to determine a position of the particular location.

14. The method of claim 11, further comprising updating the temperature and positional model based on the temperature and position information received.

15. The method of claim 11, wherein the temperature and positional model is retrieved from a memory storing a plurality of temperature and positional models each being defined based on different cooling curves associated with the paving material.

16. The method of claim 11, wherein the plurality of predicted temperatures include a tender zone, a compaction zone, and a cold zone.

17. The method of claim 16, wherein the tender zone is represented on the display by a first color filling the space between a starting location and an end location of the tender zone, and wherein the cold zone is represented on the display by a second color filling the space between the starting location and the end location of the cold zone.

18. The method of claim 16, wherein the temperature and positional model is based in part on one or more of an ambient temperature, a wind speed, weather, humidity, paving material type, and a moisture level.

19. The method of claim 16, wherein a compacting operational function is identified as being locked out in the tender zone and the cold zone.

20. A compactor, comprising:
a front ground engaging member;
a rear ground engaging member;
a power source to drive at least one of the ground engaging members; and
an operator interface configured to determine and display a predicted temperature of a paving material at a plurality of positions, the operator interface comprising:
a transceiver configured to receive temperature and position information of a portion of the paving material;
a processor in communication with the transceiver and configured to determine a plurality of predicted temperatures associated with a plurality of positions of the paving material based on a temperature and positional model and the temperature and position information; and
a display device in communication with the processor and configured to display a graphical user interface configured to receive operator input, convert the plurality of predicted temperatures of the paving material at the plurality of positions of the paving material into a map within the graphical user interface displaying a plurality of different temperature zones spatially positioned relative to at least one machine, and identify at least one operational function of the at least one machine to be locked out in at least one of the temperature zones.

* * * * *